(12) United States Patent  (10) Patent No.: US 8,284,903 B2
Yuan  (45) Date of Patent: Oct. 9, 2012

(54) FILTER AND X-RAY IMAGING SYSTEM

(75) Inventor: Ping Yuan, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 220 days.

(21) Appl. No.: 12/692,150

(22) Filed: Jan. 22, 2010

(65) Prior Publication Data

US 2010/0189216 A1     Jul. 29, 2010

(30) Foreign Application Priority Data

Jan. 24, 2009  (CN) .......................... 2009 1 0118737

(51) Int. Cl.
    *G21K 3/00*       (2006.01)
(52) U.S. Cl. ....................................... 378/158; 378/156
(58) Field of Classification Search ........... 378/156–160
    See application file for complete search history.

(56) References Cited

U.S. PATENT DOCUMENTS

| | | | |
|---|---|---|---|
| 3,156,824 A | 11/1964 | Peyser | |
| 4,246,488 A | 1/1981 | Hura | |
| 4,670,896 A | 6/1987 | Klausz | |
| 4,933,960 A | 6/1990 | Fujisaki | |
| 5,081,660 A | 1/1992 | Fujisaki | |
| 6,036,362 A | 3/2000 | Schmitt | |
| 6,305,842 B1 | 10/2001 | Kunert | |
| 6,851,854 B2 | 2/2005 | Schmitt | |
| 7,072,447 B2 | 7/2006 | Graf et al. | |
| 7,263,170 B2 | 8/2007 | Pellegrino | |
| 2002/0186817 A1 | 12/2002 | Schukalski et al. | |
| 2004/0013238 A1 | 1/2004 | Wurzer | |
| 2006/0182226 A1 | 8/2006 | Yuan et al. | |
| 2008/0279337 A1 | 11/2008 | Yuan | |

FOREIGN PATENT DOCUMENTS

JP      11-076219      3/1999

OTHER PUBLICATIONS

European Patent Office, European Search Report for Application No. 10150923.0-1265, May 17, 2010, 6 pages, EP.

*Primary Examiner* — Jurie Yun (74) *Attorney, Agent, or Firm* — Armstrong Teasdale LLP (57) ABSTRACT

A filter capable of adjusting spectrum in multiple stages and that capable of attaining the reduction of size, as well as an X-ray imaging system having such a filter, are provided. The filter, which is for adjusting the spectrum of passing radiation, comprises a support plate having an aperture for passage therethrough of radiation, plural filter plates supported by the filter plate and having mutually different filter characteristics, and moving device for moving the plural filter plates selectively to a position to close the aperture and a position to open the aperture.

20 Claims, 15 Drawing Sheets

FIG. 15 ial No. 200910118737.2 filed Jan. 24, 2009, which
FILTER AND X-RAY IMAGING SYSTEM

CROSS REFERENCE TO RELATED APPLICATIONS

This application claims the benefit of Chinese Patent Application No. 200910118737.2 filed Jan. 24, 2009, which is hereby incorporated by reference in its entirety.

BACKGROUND OF THE INVENTION

The embodiments described herein relate to a filter and an X-ray imaging system and, more particularly, to a filter for adjusting the spectrum of X-ray and an X-ray imaging system provided with such a filter.

In an X-ray imaging system, the spectrum of X-ray is adjusted by a filter and thereafter the X-ray is radiated to a subject. The filter is installed within a collimator box attached to an X-ray tube. In order to obtain a desired spectrum, plural filter plates of the filter, which are attached to a rotary disc, are used selectively (see, for example, Japanese Unexamined Patent Publication No. Hei 11 (1999)-76219 (Paragraph No. 0009, FIGS. 1 and 2)).

BRIEF DESCRIPTION OF THE INVENTION

It is desirable that the spectrum be adjustable in multiple stages. However, in the configuration wherein filter plates are switched over from one to another by device of a rotary disc, the adjustment is up to four stages at most. If an attempt is made to make adjustment possible in seven or more multiple stages in the rotary disc method, the rotary disc for the mounting of many filters becomes large-sized and thus such an attempt is not practical.

Accordingly, embodiments of the present invention provide a filter permitting the adjustment of spectrum in multiple stages and that permitting the reduction of size, as well as an X-ray imaging system provided with such a filter.

In a first aspect there is provided a filter for adjusting the spectrum of passing radiation, comprising: a support plate having an aperture for passage therethrough of radiation; a plurality of filter plates supported by the support plate and having mutually different filer characteristics; and moving device for moving the plural filter plates selectively to a position to close the aperture and a position to open the aperture.

In a second aspect there is provided, in accordance with the first aspect, a filter wherein the moving device comprises: spring device for operating the filter plates in a direction away from the aperture; a plurality of ratchets plates supported by the support plate in proximity to the filter plates and each having a notched portion; a first support point for supporting the filter plates pivotably on the support plate; a second support plate for supporting the ratchet plates pivotably on the support plate; a leaf spring connected to the filter plates and the ratchet plates, causing the filter plates and the ratchet plates to pivot interlockedly with each other; and a pawl engageable with the notched portions of the ratchet plates, the pawl being moved to pivot the ratchet plates, thereby making the filter plates movable to the position to close the aperture.

In a third aspect there is provided, in accordance with the first aspect, a filter wherein the support plate has a top layer and a bottom layer parallel to each other, and the filter plates are supported by the top layer and the bottom layer.

In a fourth aspect there is provided, in accordance with any of the first to the third aspects, a filter wherein the support plate is in the shape of disc and is formed with the apertures at a center thereof.

In a fifth aspect there is provided, in accordance with any of the first to the fourth aspects, a filter further comprising a ring capable of rotating along the circumference of the support plate, and the pawl is provided in the ring.

In a sixth aspect there is provided an X-ray imaging system for radiographing a subject with X-ray passing through a filter, the filter comprising: a support plate having an aperture for passage therethrough of radiation; a plurality of filter plates supported by the support plate and having mutually different filter characteristics; and moving device for moving the plural filter plates selectively to a position to close the aperture and a position to open the aperture.

In a seventh aspect there is provided, in accordance with the sixth aspect, an X-ray imaging system wherein the moving device comprises: spring device for operating the filter plates in a direction away from the aperture; a plurality of ratchet plates supported by the support plate in proximity to the filter plates and each having a notched portion; a first support point for supporting the filter plates pivotably on the support plate; a second support point for supporting the ratchet plates pivotably on the support plate; a leaf spring connected to the filter plates and the ratchet plates, causing the filter plates and the ratchet plates to pivot interlockedly with each other; and a pawl engageable with the notched portions of the ratchet plates, the pawl being moved to pivot the ratchet plates, thereby making the filter plates movable to the position to close the aperture.

In an eighth aspect there is provided, in accordance with the sixth aspect, an X-ray imaging system wherein the support plate has a top layer and a bottom layer parallel to each other, and the filter plates are supported by the top layer and the bottom layer.

In a ninth aspect of the present invention there is provided, in accordance with any of the sixth to eighth aspects, an X-ray imaging system wherein the support plate is in the shape of a disc and is formed with the aperture at a center thereof.

In a tenth aspect there is provided, in accordance with any of the sixth to ninth aspects, an X-ray imaging system wherein the filter further comprises a ring capable of rotating along the circumference of the support plate, and the pawl is provided in the ring.

According some embodiments, since the filter for adjusting the spectrum of passing radiation comprises: a support plate having an aperture for passage therethrough of radiation; a plurality of filter plates supported by the support plate and having mutually different filter characteristics; and moving device for moving the plural filter plates selectively to a position to close the aperture and a position to open the aperture, it is possible to realize a filter capable of adjusting the spectrum in multiple stages and capable of attaining the reduction of size, as well as an X-ray imaging system provided with such a filter.

DETAILED DESCRIPTION OF THE INVENTION

Embodiments of the present invention will be described in detail hereinunder with reference to the drawings. The present invention is not limited to the embodiments described herein.

Figure 1:
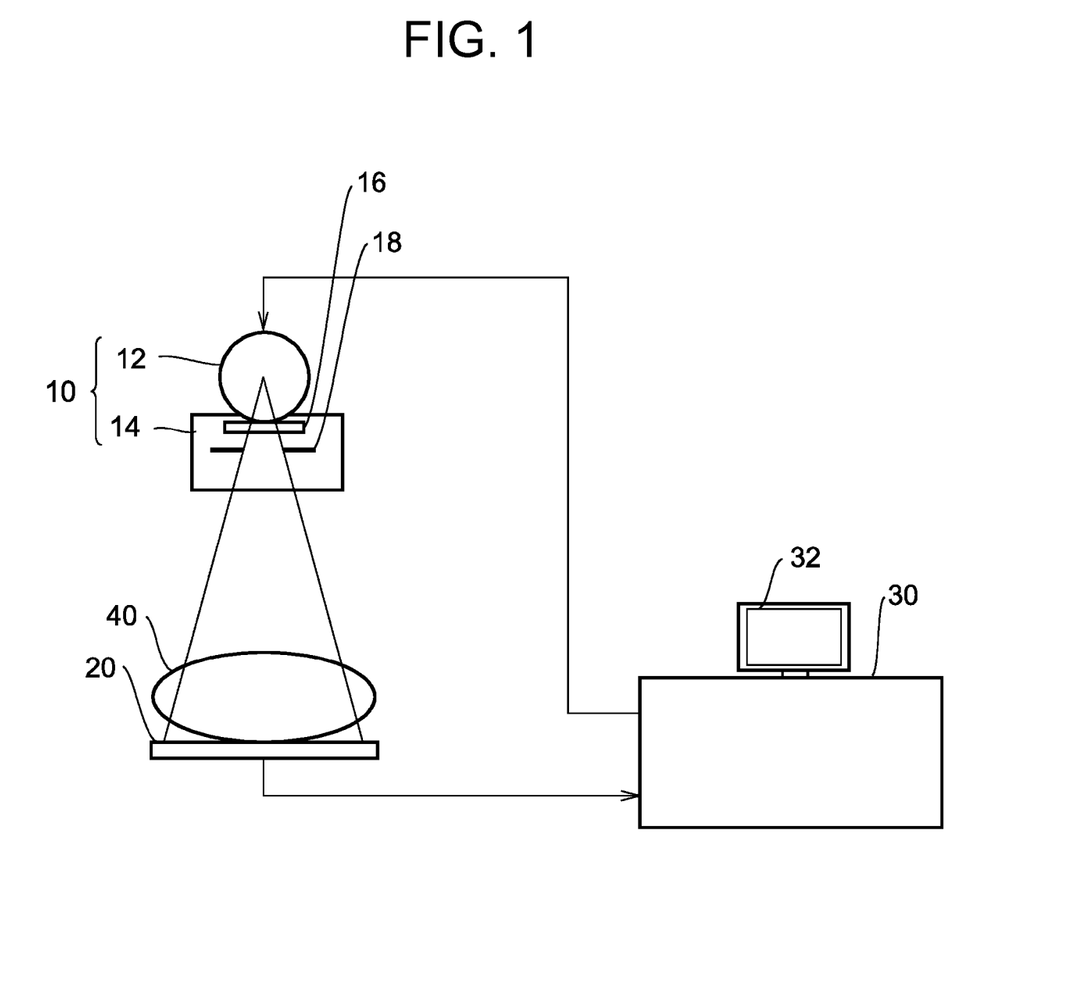
FIG. 1 is a diagram showing the configuration of an X-ray imaging system as an example of the best mode for carrying out the invention.

FIG. 1 shows a schematic configuration of an X-ray imaging system.

AS shown in the same figure, this system includes an X-ray irradiator 10, an X-ray detector 20 and an operator console 30. The X-ray irradiator 10 and the X-ray detector 20 are opposed to each other with a subject 40 therebetween.

The X-ray irradiator 10 includes an X-ray tube 12 and a collimator box 14. A filter 16 and a collimator 18 are accommodated within the collimator box 14. The filter 16 is an example of the best mode for carrying out the invention. With the configuration of the filter 16 there is shown an example of the best mode for carrying out the invention with respect to the filter.

X-ray emitted from the X-ray tube 12 is adjusted its spectrum by the filter 16 and is then radiated to the subject 40 through an aperture of the collimator 18. The filter 16 is a spectrum variable filter. The collimator 18 is an aperture variable collimator.

The X-ray which has passed through the subject 40 is detected by the X-ray detector 20 and is inputted to the operator console 30. On the basis of the inputted signal the operator console 30 reconstructs a radioscopic image of the subject 40. The reconstructed image is displayed on a display 32 of the operator console 30.

The operator console 30 controls the X-ray irradiator 10. Control of the filer 16 and that of the collimator 18 are included in the control of the X-ray irradiator 10 made by the operator console 30. Where required, the filter 16 and the collimator 18 can be adjusted manually.

Figure 2:
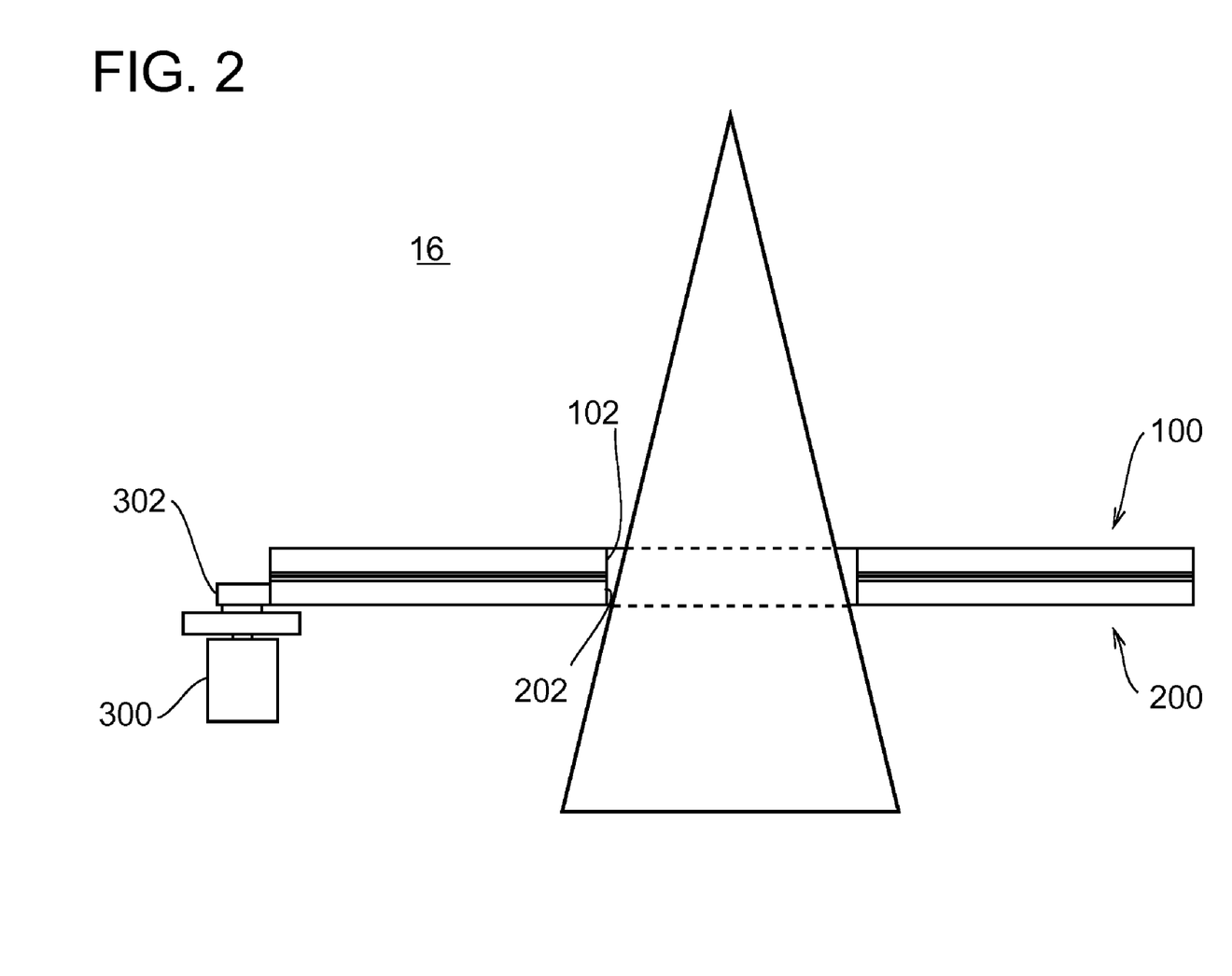
FIG. 2 is a diagram showing a schematic configuration of a filter.

FIG. 2 shows the configuration of the filter 16 schematically. As shown in FIG. 2, the filter 16 is of a two-layer structure comprising a top layer 100 and a bottom layer 200. The top layer 100 has an aperture 102 and the bottom layer 200 has an aperture 202. The apertures 102 and 202 are concentric and equal in size and X-ray passes through the apertures 102 and 202.

The top layer 100 and the bottom layer 200 each have on the outer periphery thereof such a ring as will be described later. The rings are integrally driven by a motor 300 via a gear 302 so as to be rotatable reversibly in clockwise and counterclockwise directions.

Figure 3:
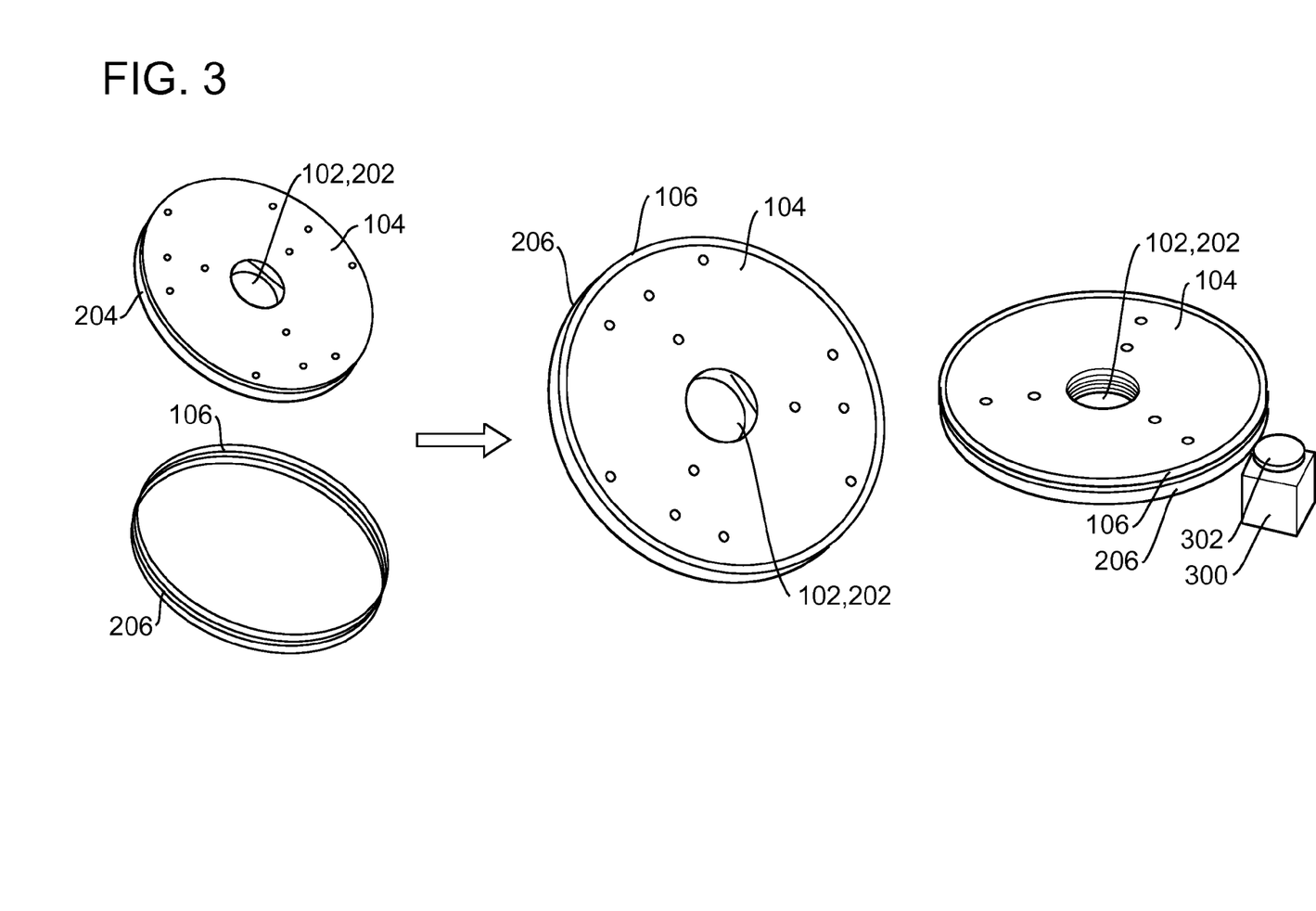
FIG. 3 is a diagram showing a schematic configuration of the filter.

FIG. 3 shows a ring-detached state and a ring-attached state with respect to the top layer 100 and the bottom layer 200. As shown in FIG. 3, the top layer 100 and the bottom layer 200 include disc-like top support 104 and bottom support 204 assembled together in facing relation to each other, as well as rings 106 and 206 attached respectively to their outer peripheries in a rotatable manner.

The top support 104 and the bottom support 204 do not rotate and are formed with the apertures 102 and 202 respectively at their centers. The rings 106 and 206 are integrally driven by the motor 300 via the gear 302 and are adapted to rotate along the circumference of the top support 104 and that of the bottom support 204 respectively.

Figure 4:
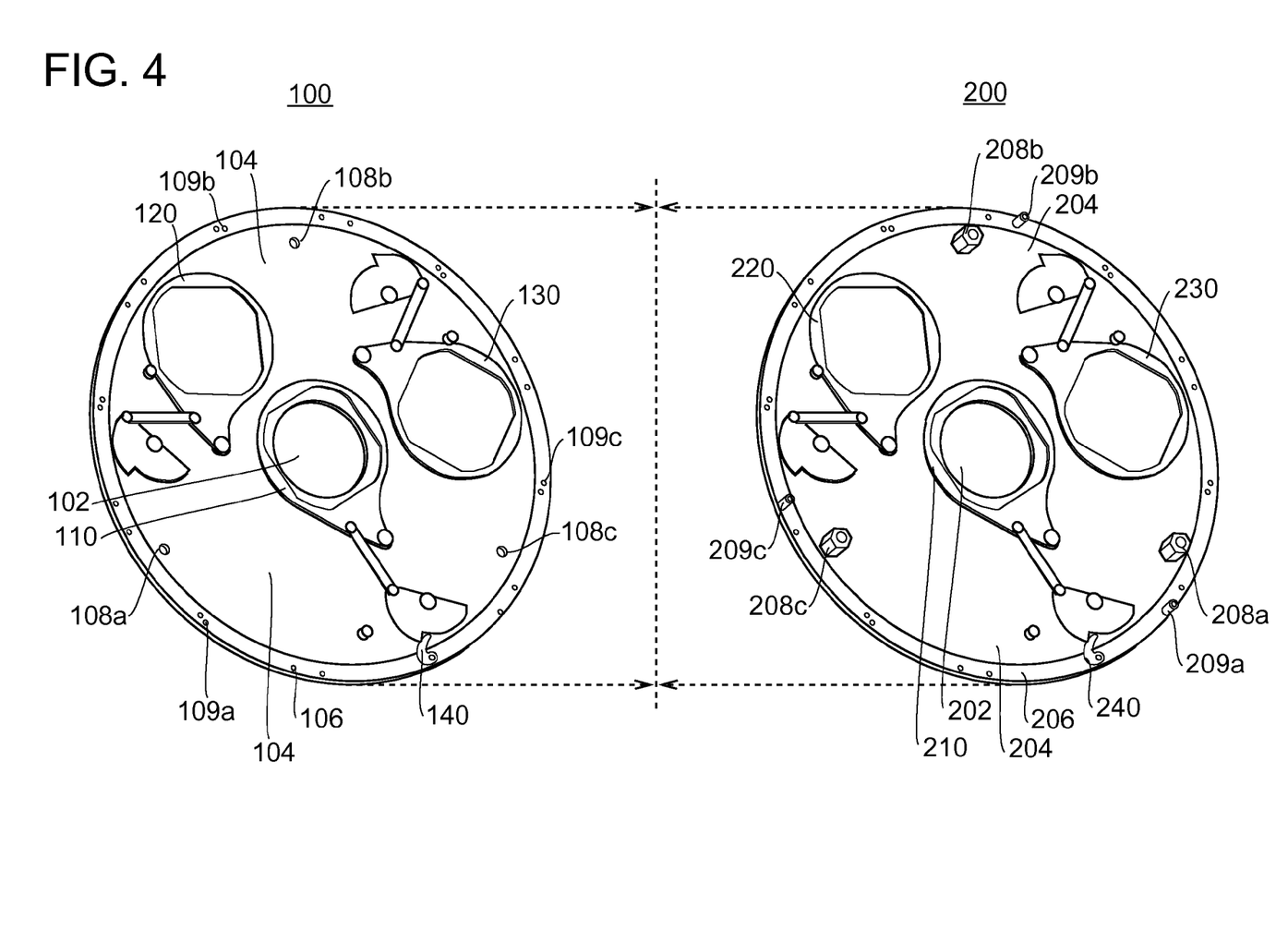
FIG. 4 is an exploded diagram showing the configuration of the filter.

FIG. 4 shows a disassembled state of the filter 16 into the top layer 100 and the bottom layer 200. FIG. 4 shows a state in which the top support 104 and the bottom support 204 are opened to both right and left at the confronting portion thereof.

The top support 104 and the bottom support 204 are coupled together by three holes 108a, 108b, 108c formed in the top support 104 and three studs 208a, 208b, 208c formed on the bottom support 104.

The rings 106 and 206 are coupled together by three holes 109a, 109b, 109c formed in the ring 106 and three studs 209a, 209b, 209c formed on the ring 206.

The top support 104 has three filter plates 110, 120 and 130 on an inner surface thereof, i.e., on its surface confronting the bottom support 204. The filter plates 110, 120 and 130 comprise three steel plates or the like different in thickness and supported by a support frame. For example, the three steel plates or the like are 0.1, 0.2 and 0.3 mm, respectively, in thickness.

The filter plates 110, 120 and 130 constitute a part of three parallel link mechanisms, and with operation of the parallel links, the filter plates are adapted to advance and retreat to a position to close the aperture 120 and a position to open the same aperture.

The three parallel links are driven in order by a pawl 140 which rotates together with the ring 106. Here there is shown a state in which with operation of the pawl 140 the filter plate 110 has advanced to the position to close the aperture 102, while the filter plates 120 and 130 have retreated to the position to open the aperture 102.

The bottom support 204 has three filter plates 210, 220 and 230 on an inner surface thereof, i.e., on its surface confronting the top support 104. The filter plates 210, 220 and 230 comprise three steel plates or the like different in thickness and supported by a support frame. For example, the three steel plates or the like are 0.6, 0.9 and 1.5 mm, respectively, in thickness.

The filter plates 210, 220 and 230 constitute a part of the three parallel links, and with operation of the parallel links, the filter plates are adapted to advance and retreat to a position to close the aperture 202 and a position to open the same aperture.

The three parallel links are driven in order by a pawl 240 which rotates together with the ring 206. Here there is shown a state in which with operation of the pawl 240 the filter plate 210 has advanced to the position to close the aperture 202, while the filter plates 220 and 230 have advanced to the position to open the aperture 202.

Figure 5A:
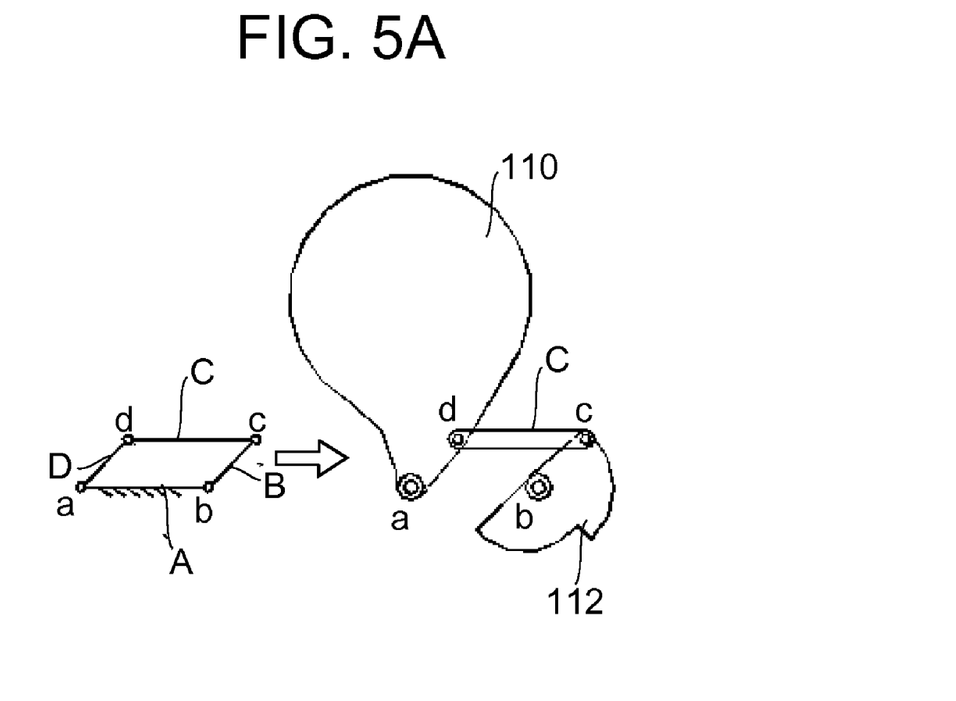
FIGS. 5A and 5B are diagrams showing the configuration and operation of parallel links
Figure 5B:
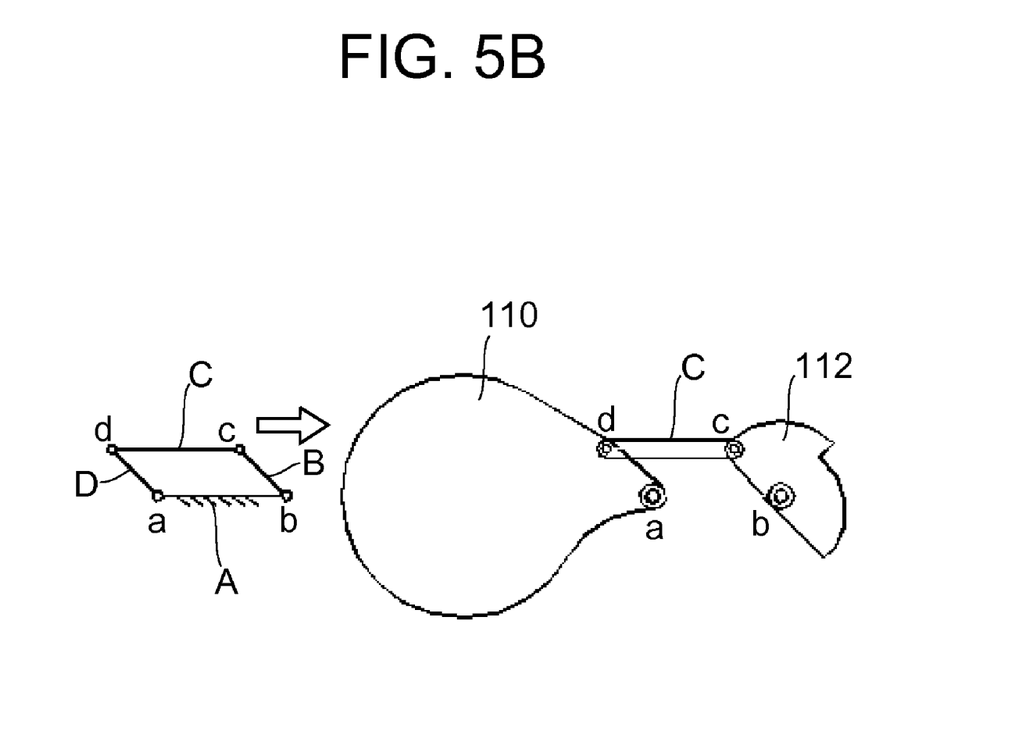

FIGS. 5A and 5B show the configuration and operation of parallel links with respect to the filter plate 110. Also as to the other filter plates 120 to 230, the configuration and operation of parallel links are the same. As shown in FIGS. 5A and 5B, the parallel links are made up of links A, B, C, D and joints a, b, c, d. The link A is a fixed link, the link B is a driving link, the link C is a parallel moving link, and the link D is a driven link.

The driven link D is constituted by the filter plate 110 and the driving link B is constituted by a ratchet plate 112. The filter plate 110 is rotatable about the joint a, the ratchet plate 112 is rotatable about the joint b, and both are connected together at the joints c and d through the link C.

With such an operation of the parallel links, the filter plate 110 assumes either such a retreated state as FIG. 5A or such an advanced state as FIG. 5B. The filter plate 110, in its retreated state FIG. 5A, opens the aperture 102, while in its advanced state FIG. 5B it closes the aperture 102.

Figure 6A:
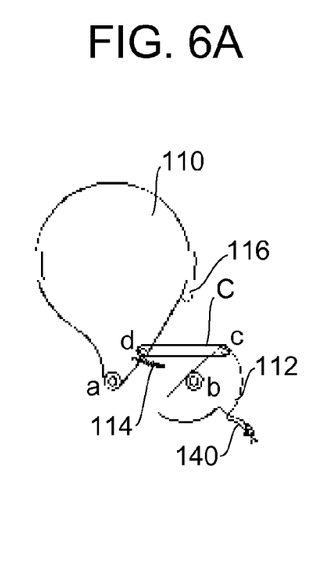
FIGS. 6A, 6B, and 6C are diagrams showing the configuration and operation of the parallel links.
Figure 6B:
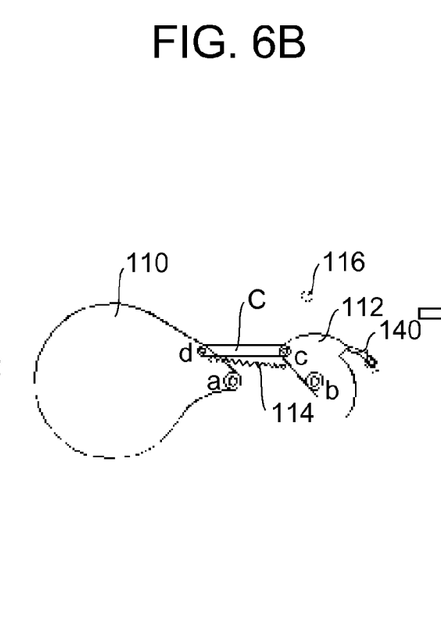
Figure 6C:
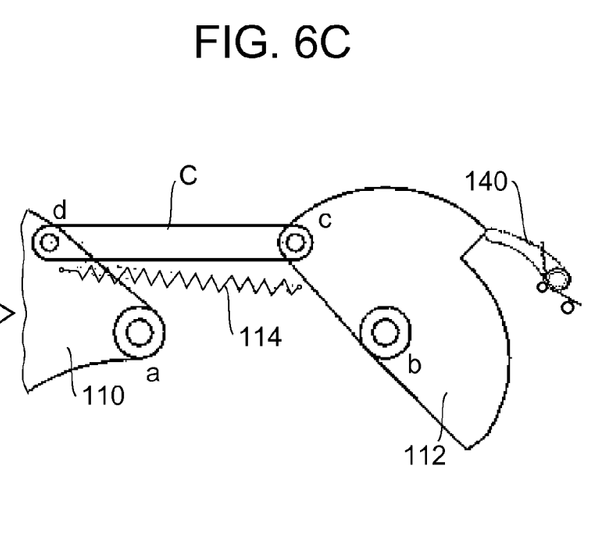

As shown in FIGS. 6A, 6B, and 6C, a tensile force induced by a spring 114 acts on the filter plate 110 constantly. Consequently, while the parallel links are not in operation, the filter plate 110 is in abutment against a stop pin 116, as shown in FIG. 6A.

The parallel links operate when the ratchet plate 112 is pushed up by the pawl 140. The pawl 140 rotates while describing a circular path together with the ring 106 and pushes up the ratchet plate 112 when it rotates in the counterclockwise direction, thereby causing rotation of the ratchet plate 112. As a result, the parallel links operate and the filter plate 110 advances to the position to close the aperture 102, as shown in FIG. 6B. The engagement between the ratchet plate 112 and the pawl 140 in this state is as shown on a larger scale in FIG. 6C.

Figure 7:
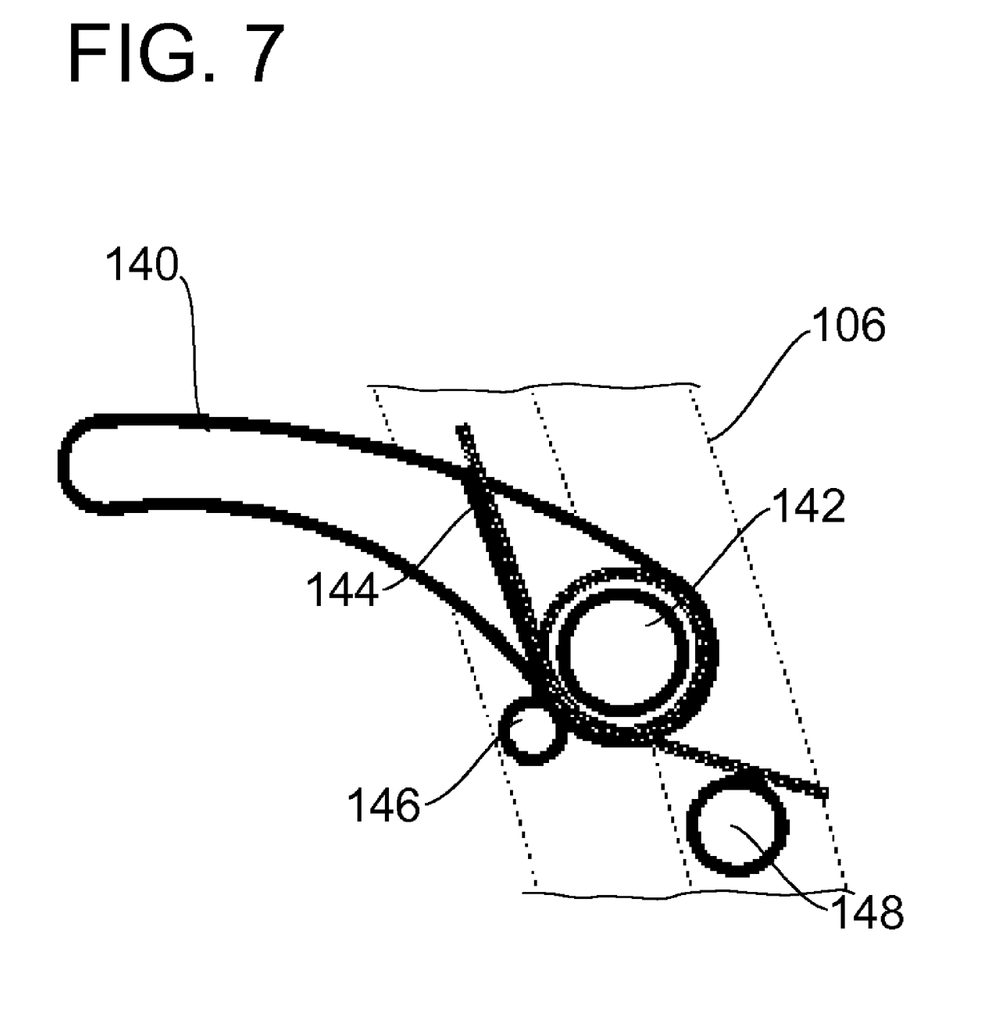
FIG. 7 is a diagram showing the configuration of a pawl.

As shown in FIG. 7, the pawl 140 is attached to the ring 106 rotatably with a shaft 142. A rotating force is applied in the counterclockwise direction in the figure by means of a coil spring 144 mounted on the shaft 142 and the pawl 140 is in an abutted state against a stop pin 146. One end of the coil spring 144 is fixed to the pawl 140 and an opposite end thereof is fixed to a pin 148.

When the pawl 140 stays at the position b as shown in FIGS. 6A, 6B, and 6C, the filter plate 110 stays at its advanced position. As the pawl 140 further moves in the counterclockwise direction from this state, the pawl 140 passes while pushing aside the ratchet plate 112. At this time, with the restoring force of the spring 114, the filter plate 110 retreats and the aperture 102 is opened.

When the ring 106 rotates in the clockwise direction, the pawl 140 cannot push up the ratchet plate 112, so that the ratchet plate 112 is not actuated and hence the parallel links do not operate.

A description will now be given about a synthetic operation of the filter 16 thus constructed. Behaviors of the filter plates with rotation of the pawls 140 and 240 are shown in order in FIGS. 8 to 14. FIGS. 8 to 14 are diagrams in which the top layer 100 and the bottom layer 200 are seen in an X-ray irradiating direction.

Figure 8:
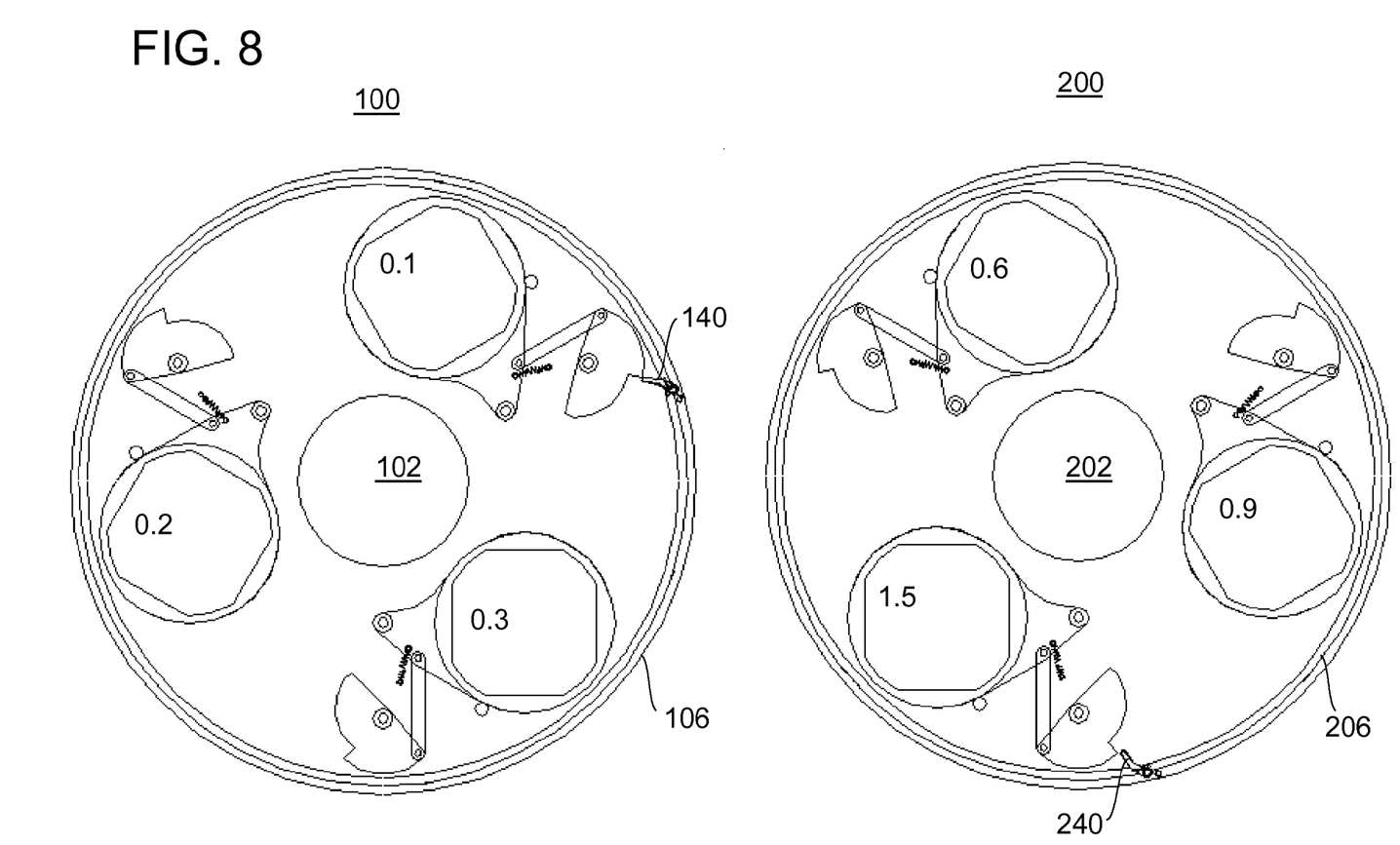
FIG. 8 is a diagram showing an operating condition of the filter.

FIG. 8 shows an initial state of both top layer 100 and bottom layer 200. In the initial state, none of the filter plates close the apertures 102 and 202. This corresponds to the state in which a filter plate having a thickness of zero has been inserted into the apertures 102 and 202.

Figure 9:
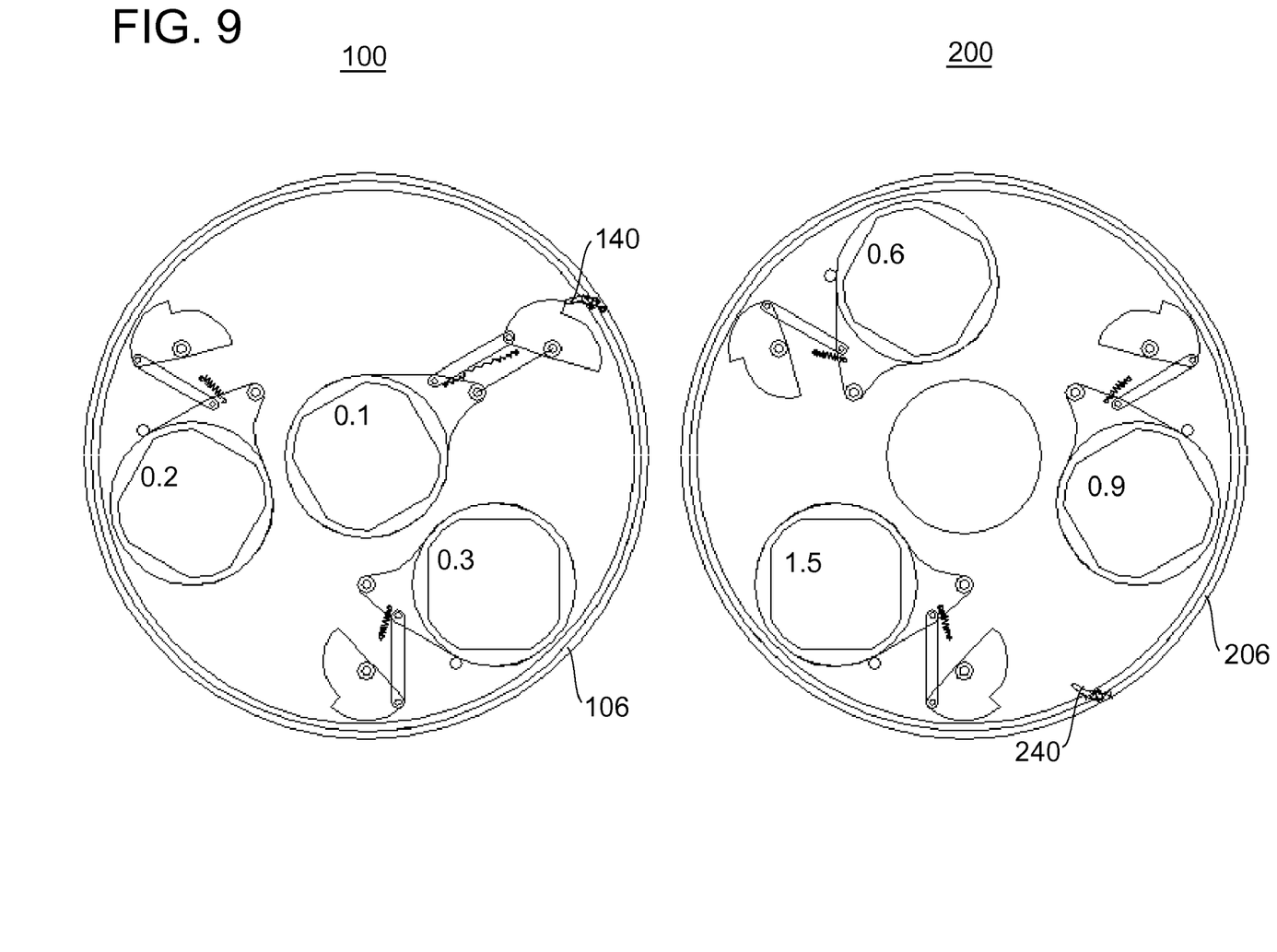
FIG. 9 is a diagram showing a further operating condition of the filter.
Figure 10:
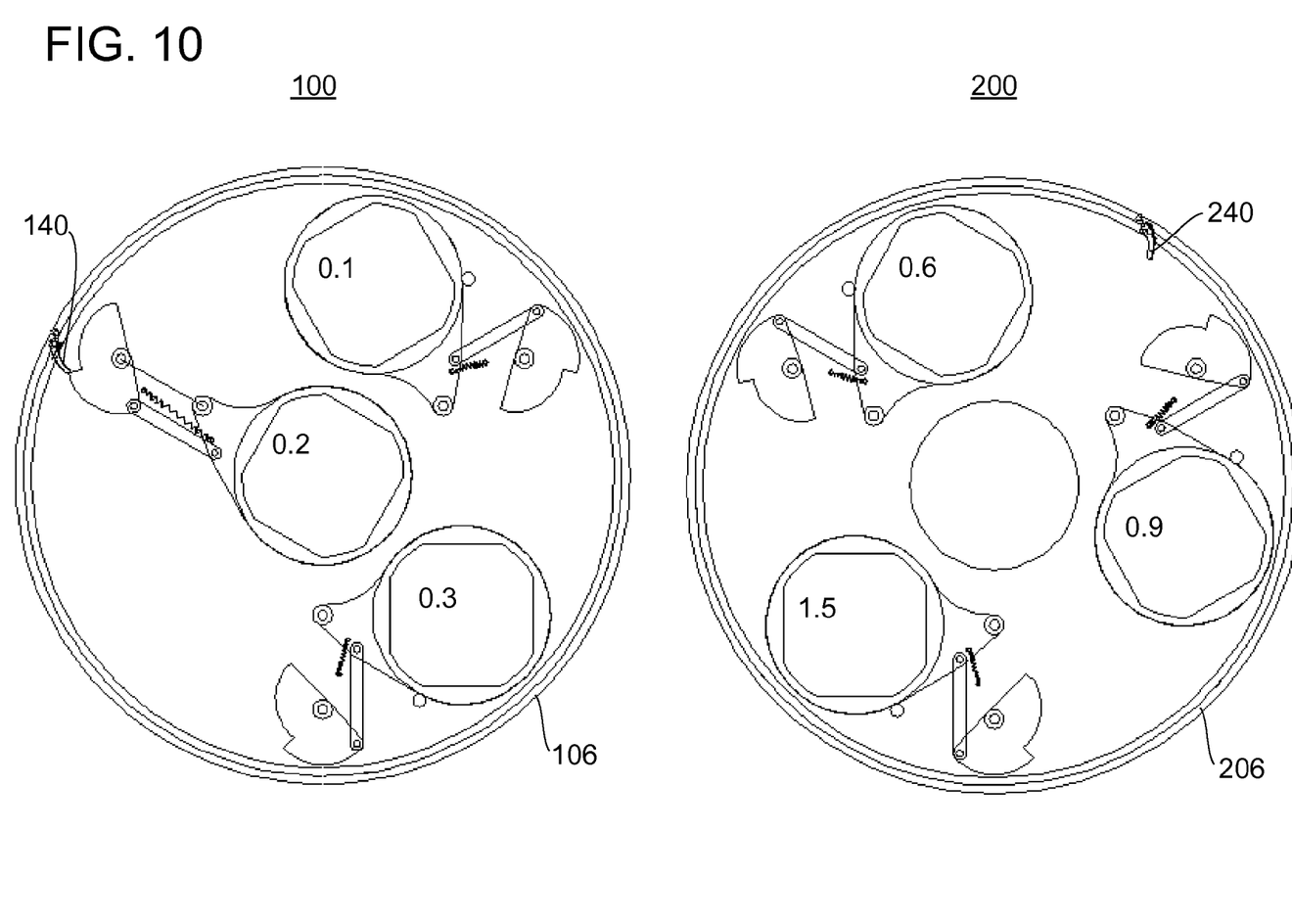
FIG. 10 is a diagram showing a still further operating condition of the filter.
Figure 11:
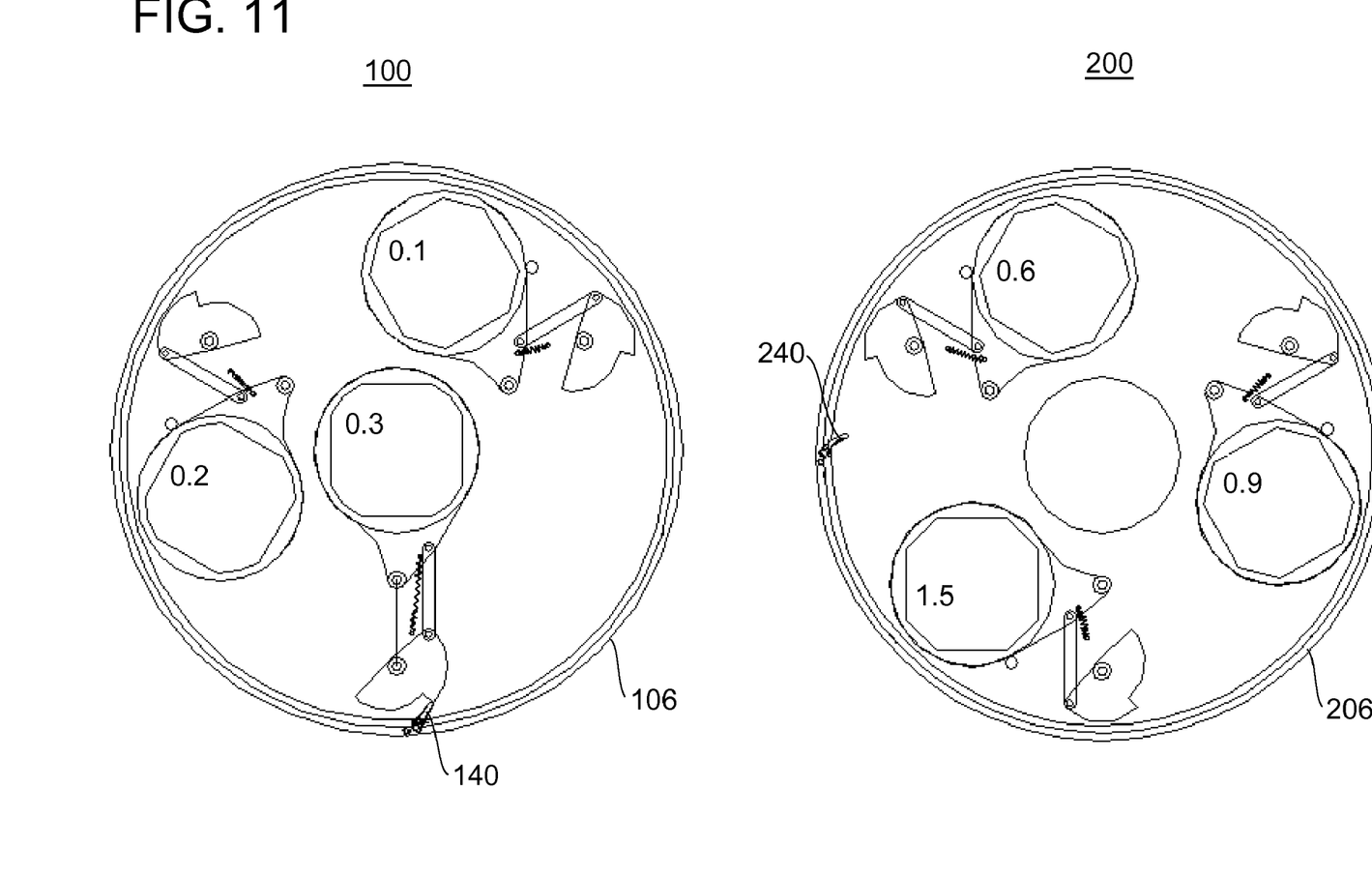
FIG. 11 is a diagram showing a still further operating condition of the filter.

With counterclockwise rotation of the rings 106 and 206 and with drive by the pawl 140, filter plates 0.1, 0.2 and 0.3 located on the top player 100 side advance in order to the position to close the aperture 102, as shown in FIGS. 9, 10 and 11. In this way X-ray spectrum is adjusted by each of the filter plates. During this period, on the bottom layer 200 side, all the filter plates stay in their retreated positions because the pawl 240 passes while stroking all the ratchet plates.

Figure 12:
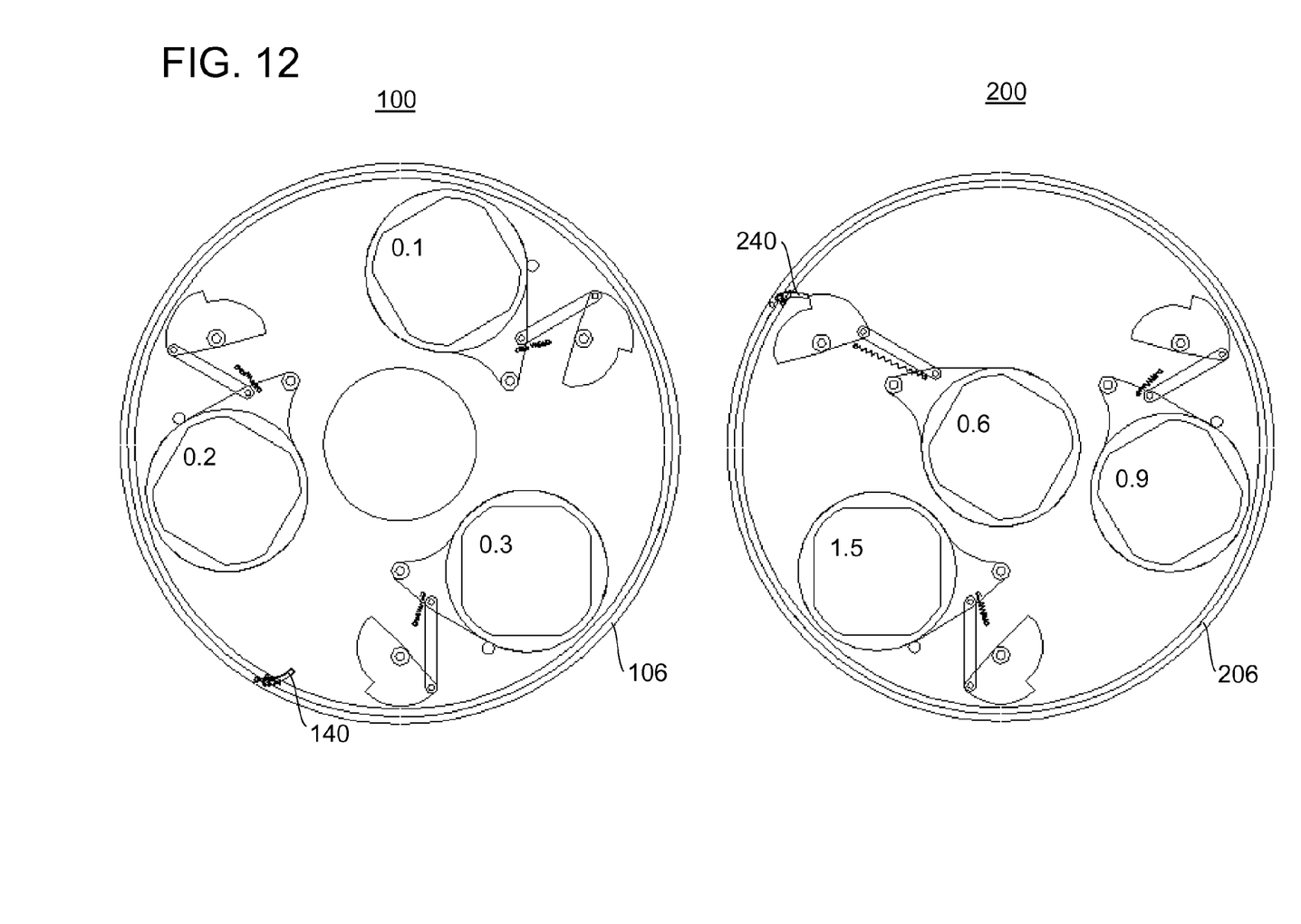
FIG. 12 is a diagram showing a still further operating condition of the filter.
Figure 13:
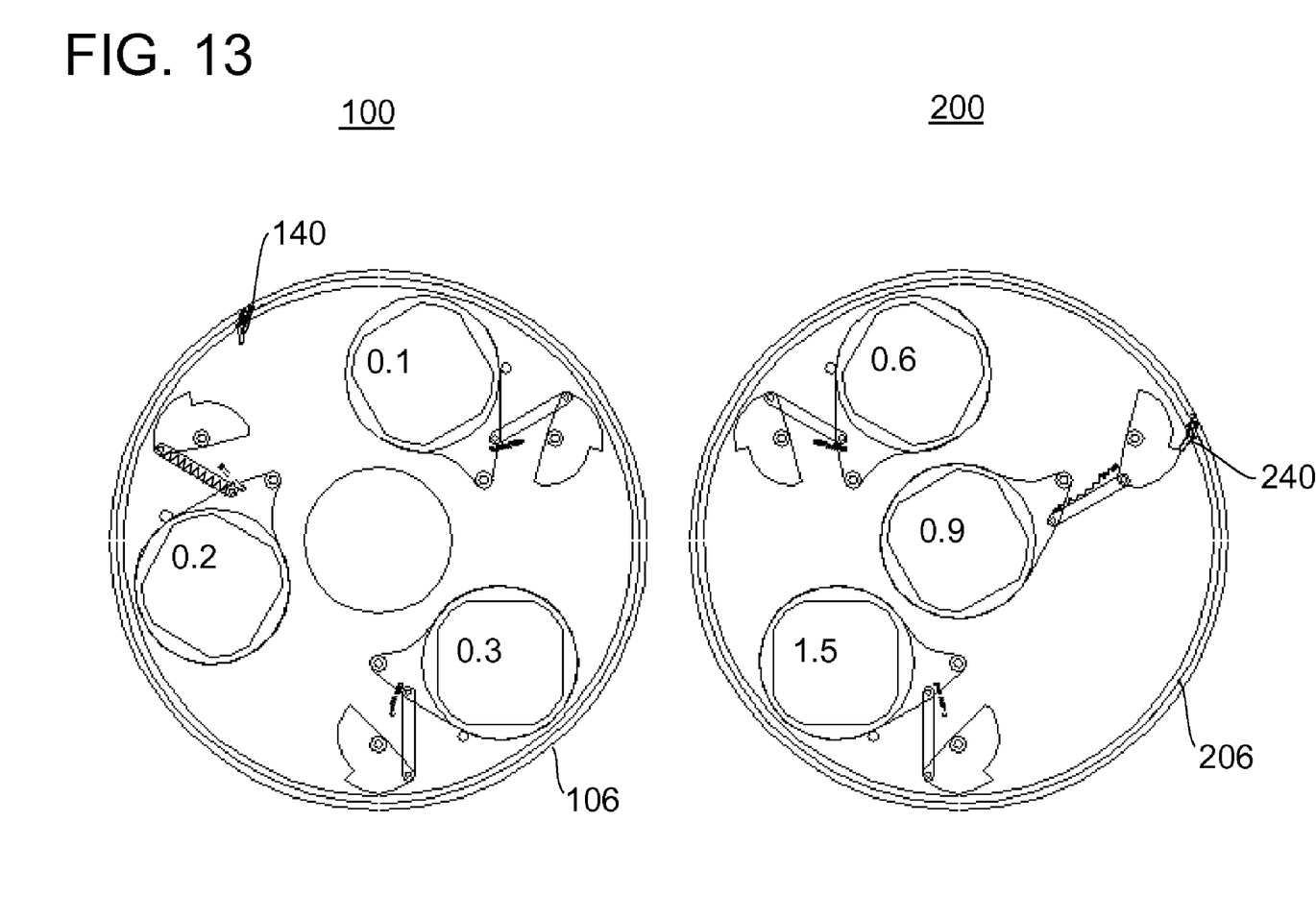
FIG. 13 is a diagram showing a still further operating condition of the filter.
Figure 14:
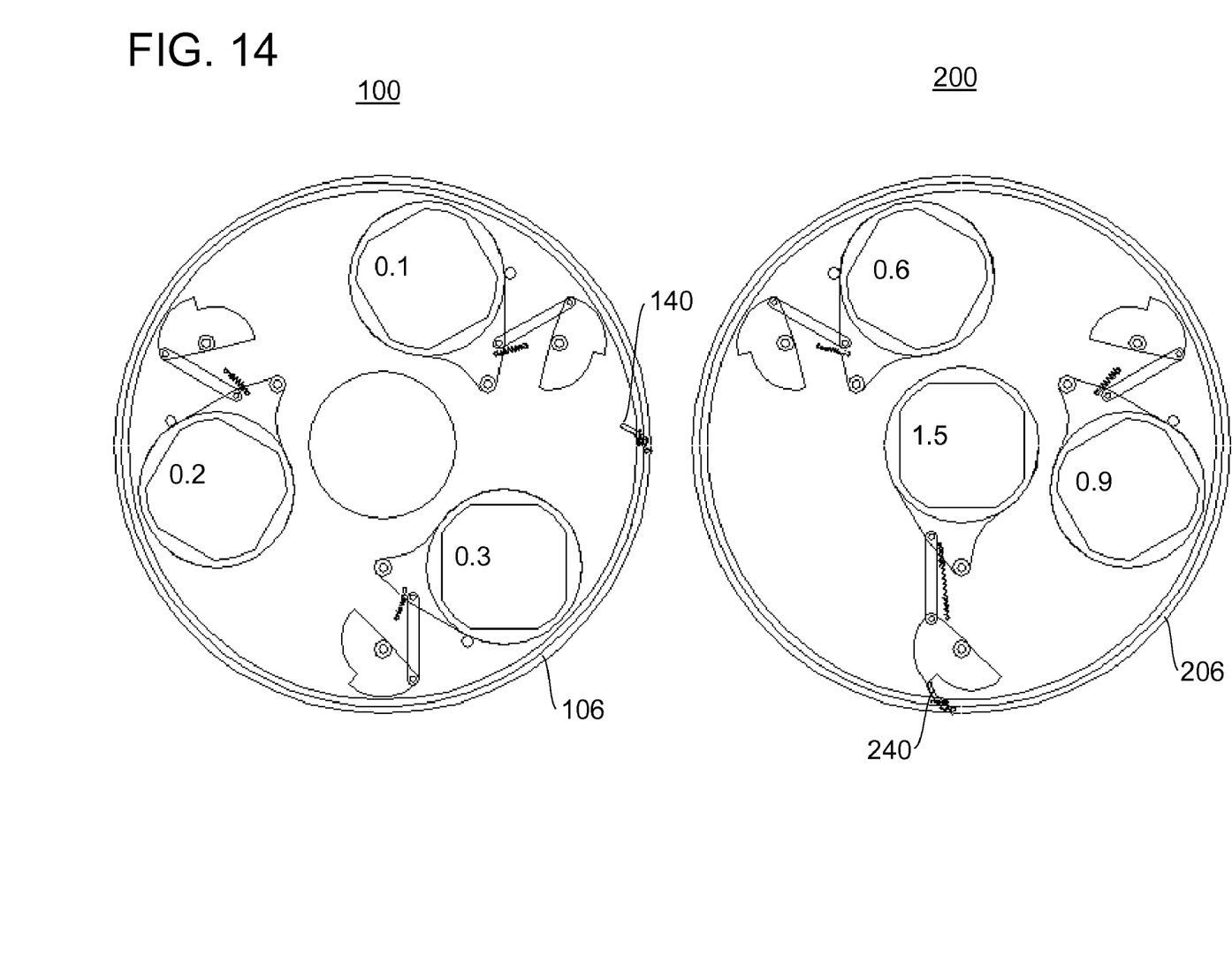
FIG. 14 is a diagram showing a still further operating condition of the filter.

With clockwise rotation of the rings 106 and 206 and with drive by the pawl 240, filter plates 0.6, 0.9 and 1.5 located on the bottom layer 200 side advance in order to the position to close the aperture 202, as shown in FIGS. 12, 13 and 14. In this way X-ray spectrum is adjusted by each of the filter plates. During this period, on the top layer 100 side, all the filter plates stay in their retreated positions because the pawl 140 passes while stroking all the ratchet plates.

In this way it is possible to obtain the filter 16 whose filter plate thickness changes in seven stages. The filter 16 has a two-layer structure of both top layer 100 and bottom layer 200, and each layer has three filter plates driven by parallel links, thus facilitating reduction of the entire size.

Figure 15:
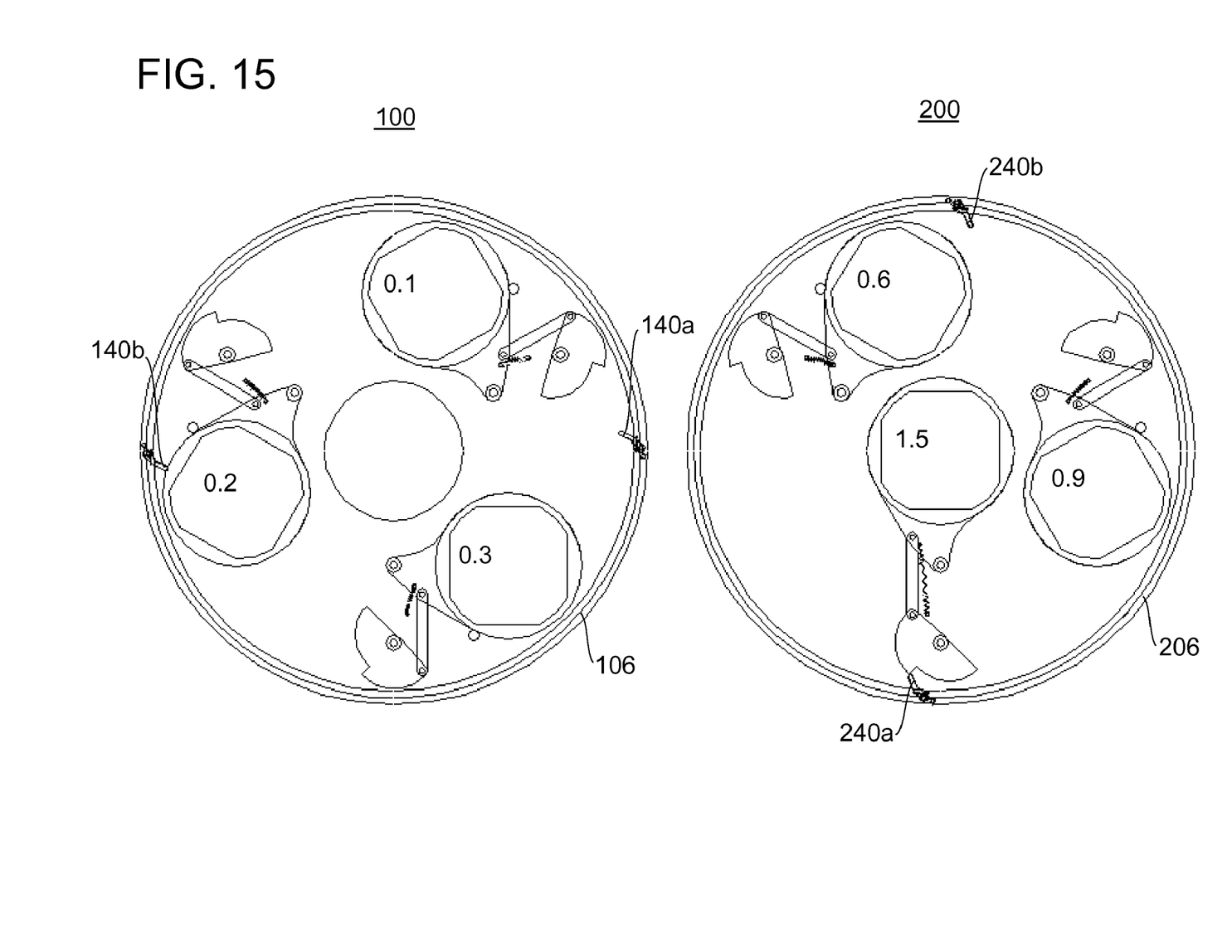
FIG. 15 is a diagram showing a still further operating condition of the filter.

Two pawls for actuating parallel links may be provided for each layer as in FIG. 15. With two pawls 140a and 140b and 240a and 240b, it is possible to shorten the time for access to the filter plate located at the remotest position from the current position of each pawl.

When the number of switching stages of filter plates may be four, the filter 16 may be of a single-layer structure of either the top layer 100 or the bottom layer 200. Further, the number of filter plates per layer is not limited to three, but may be any other suitable number.

What is claimed is:

1. A filter for use in adjusting a spectrum of passing radiation, said filter comprising:
    a support plate having an aperture for passage therethrough of radiation, the support plate being disc-shaped and having a circumference;
    a plurality of filter plates supported by the support plate within the circumference and having mutually different filter characteristics; and
    a moving device configured to selectively move the plurality of filter plates to a first position to close the aperture and a second position to open the aperture, the moving device configured to bias the plurality of filter plates to the second position and to extend the plurality of filter plates radially inwardly toward the first position.

2. A filter according to claim 1, wherein the moving device comprises:
    a spring device configured to operate the plurality of filter plates in a direction away from the aperture;
    a plurality of ratchet plates supported by the support plate in proximity to the plurality of filter plates, each of the plurality of ratchet plates comprising a notched portion;
    a first support point positioned to pivotably support the plurality of filter plates on the support plate;
    a second support point positioned to pivotably support the plurality of ratchet plates on the support plate;
    a leaf spring connected to the plurality of filter plates and the plurality of ratchet plates, the leaf spring configured to cause the plurality of filter plates and the plurality of ratchet plates to pivot interlockedly with each other; and
    a pawl engageable with the notched portion of each of the plurality of ratchet plates, the pawl configured to move in order to pivot the plurality of ratchet plates, thereby making the plurality of filter plates movable to the first position to close the aperture.

3. A filter according to claim 2, wherein the support plate is formed with the aperture at a center thereof.

4. A filter according to claim 2, further comprising a ring configured to rotate along the circumference of the support plate, the ring comprising the pawl.

5. A filter according to claim 1, wherein the support plate comprises a top layer and a bottom layer parallel to each other, and the plurality of filter plates are supported by the top layer and the bottom layer.

6. A filter according to claim 5, wherein the support plate is formed with the aperture at a center thereof.

7. A filter according to claim 5, further comprising a ring configured to rotate along the circumference of the support plate, the ring comprising a pawl.

8. A filter according to claim 1, wherein the support plate is formed with the aperture at a center thereof.

9. A filter according to claim 8, further comprising a ring configured to rotate along the circumference of the support plate, the ring comprising a pawl.

10. A filter according to claim 1, further comprising a ring configured to rotate along the circumference of the support plate, the ring comprising a pawl.

11. An X-ray imaging system for use in radiographing a subject with X-ray passing through a filter, the X-ray imaging system comprising:
  an X-ray irradiator; and
  a filter positioned with respect to the X-ray irradiator, the filter comprising:
    a support plate having an aperture for passage therethrough of radiation, the support plate being disc-shaped and having a circumference;
    a plurality of filter plates supported by the support plate within the circumference and having mutually different filter characteristics; and
    a moving device configured to selectively move the plurality of filter plates to a first position to close the aperture and a second position to open the aperture, the moving device configured to bias the plurality of filter plates to the second position and to extend the plurality of filter plates radially inwardly toward the first position.

12. An X-ray imaging system according to claim 11, wherein the moving device comprises:
  a spring device configured to operate the plurality of filter plates in a direction away from the aperture;
  a plurality of ratchet plates supported by the support plate in proximity to the plurality of filter plates, each of the plurality of ratchet plates comprising a notched portion;
  a first support point positioned to pivotably support the plurality of filter plates on the support plate;
  a second support point positioned to pivotably support the plurality of ratchet plates on the support plate;
  a leaf spring connected to the plurality of filter plates and the plurality of ratchet plates, the leaf spring configured to cause the plurality of filter plates and the plurality of ratchet plates to pivot interlockedly with each other; and
  a pawl engageable with the notched portion of each of the plurality of ratchet plates, the pawl configured to move in order to pivot the plurality of ratchet plates, thereby making the plurality of filter plates movable to the first position to close the aperture.

13. An X-ray imaging system according to claim 12, wherein the support plate is formed with the aperture at a center thereof.

14. An X-ray imaging system according to claim 12, wherein the filter further comprises a ring configured to rotate along the circumference of the support plate, the ring comprising the pawl.

15. An X-ray imaging system according to claim 11, wherein the support plate comprises a top layer and a bottom layer parallel to each other, and the plurality of filter plates are supported by the top layer and the bottom layer.

16. An X-ray imaging system according to claim 15, wherein the support plate is formed with the aperture at a center thereof.

17. An X-ray imaging system according to claim 15, wherein the filter further comprises a ring configured to rotate along the circumference of the support plate, the ring comprising a pawl.

18. An X-ray imaging system according to claim 11, wherein the support plate is formed with the aperture at a center thereof.

19. An X-ray imaging system according to claim 18, wherein the filter further comprises a ring configured to rotate along the circumference of the support plate, the ring comprising a pawl.

20. An X-ray imaging system according to claim 11, wherein the filter further comprises a ring configured to rotate along the circumference of the support plate, the ring comprising a pawl.

* * * * *